(12) United States Patent
Landy, III et al.

(10) Patent No.: US 10,507,292 B2
(45) Date of Patent: Dec. 17, 2019

(54) RAPID INFUSER WITH VACUUM RELEASE VALVE

(71) Applicant: Belmont Instrument, LLC, Billerica, MA (US)

(72) Inventors: John J. Landy, III, Billerica, MA (US); George G. Brusard, Lowell, MA (US); Tristan Dion, Billerica, MA (US)

(73) Assignee: Belmont Instrument, LLC, Billerica, MA (US)

( * ) Notice: Subject to any disclaimer, the term of this patent is extended or adjusted under 35 U.S.C. 154(b) by 412 days.

(21) Appl. No.: 15/364,532

(22) Filed: Nov. 30, 2016

(65) Prior Publication Data

US 2018/0147369 A1 May 31, 2018

(51) Int. Cl.
| | | |
|---|---|---|
| *H05B 6/10* | (2006.01) | |
| *A61F 5/44* | (2006.01) | |
| *A61F 7/12* | (2006.01) | |
| *A61M 5/44* | (2006.01) | |
| *A61M 5/142* | (2006.01) | |
| *A61M 5/36* | (2006.01) | |
| *A61M 5/168* | (2006.01) | |

(52) U.S. Cl.
CPC .............. *A61M 5/44* (2013.01); *A61M 5/142* (2013.01); *A61M 5/16831* (2013.01); *A61M 5/36* (2013.01); *H05B 6/108* (2013.01)

(58) Field of Classification Search
CPC .......... A61M 5/44; A61M 5/142; A61M 5/36; H05B 6/108
USPC ......... 219/629, 635, 50, 630, 667, 676, 607; 219/628, 670; 604/6.13, 6.08, 29, 291, 604/508; 607/108, 13, 114, 103, 104, 607/105, 21; 606/24, 27, 28; 700/299, 700/300; 392/470–490; 210/252, 258, 210/321.6, 321.65, 645, 646
See application file for complete search history.

(56) References Cited

U.S. PATENT DOCUMENTS

| | | |
|---|---|---|
| 1,656,518 A | 1/1928 | Hammers |
| 2,494,716 A | 1/1950 | McMahon et al. |
| 2,550,584 A | 4/1951 | Mittelmann |
| 2,886,771 A | 5/1959 | Vincent |
| 3,046,378 A | 7/1962 | Holz |
| 3,315,681 A | 4/1967 | Poppendiek |
| 3,388,230 A | 6/1968 | Cunningham et al. |
| 3,399,536 A | 9/1968 | Walz |

(Continued)

FOREIGN PATENT DOCUMENTS

| | | |
|---|---|---|
| DE | 4241830 A1 | 6/1994 |
| WO | WO-9217040 A1 | 10/1992 |

(Continued)

OTHER PUBLICATIONS

International Search Report, PCT/US2017/063612 (Rapid Infuser With Advantageous Flow Path for Blood and Fluid Warming, and Associated Components, Systems, and Methods, filed Nov. 29, 2017), issued by ISA/US, 6 pages, dated May 9, 2018.

(Continued)

*Primary Examiner* — Quang T Van
(74) *Attorney, Agent, or Firm* — Choate, Hall & Stewart LLP

(57) ABSTRACT

Presented herein is an infusate heating system with a vacuum release valve that obviates a system halt failure due to inaccurate detection of fluid level in an infusate reservoir.

21 Claims, 16 Drawing Sheets

(56) References Cited

U.S. PATENT DOCUMENTS

| | | |
|---|---|---|
| 3,443,060 A | 5/1969 | Smith |
| 3,475,590 A | 10/1969 | Pins |
| 3,482,575 A | 12/1969 | Claff et al. |
| 3,485,245 A | 12/1969 | Lahr et al. |
| 3,518,393 A | 6/1970 | Besseling et al. |
| 3,590,215 A | 6/1971 | Anderson et al. |
| 3,614,385 A | 10/1971 | Horstmann |
| 3,640,283 A | 2/1972 | Bhatia et al. |
| 3,641,302 A | 2/1972 | Sargeant |
| 3,812,315 A | 5/1974 | Martin |
| 3,816,687 A | 6/1974 | Heitner |
| 3,834,372 A | 9/1974 | Turney |
| 3,853,479 A | 12/1974 | Talonn et al. |
| 4,032,740 A | 6/1977 | Mittelmann |
| 4,038,519 A | 7/1977 | Foucras |
| 4,061,141 A | 12/1977 | Hyden et al. |
| 4,089,176 A | 5/1978 | Ashe |
| 4,108,146 A | 8/1978 | Golden |
| 4,167,663 A | 9/1979 | Granzow, Jr. et al. |
| 4,191,182 A | 3/1980 | Popovich et al. |
| 4,293,762 A | 10/1981 | Ogawa |
| 4,309,592 A | 1/1982 | Le Boeuf |
| 4,314,143 A | 2/1982 | Bilstad et al. |
| 4,321,918 A | 3/1982 | Clark, II |
| 4,322,275 A | 3/1982 | Jain |
| 4,341,936 A | 7/1982 | Virgin |
| 4,356,383 A | 10/1982 | Dahlberg et al. |
| 4,381,004 A | 4/1983 | Babb |
| 4,384,578 A | 5/1983 | Winkler |
| 4,464,563 A | 8/1984 | Jewett |
| 4,479,798 A | 10/1984 | Parks |
| 4,511,777 A | 4/1985 | Gerard |
| 4,532,414 A | 7/1985 | Shah et al. |
| 4,540,401 A | 9/1985 | Marten |
| 4,560,849 A | 12/1985 | Migliori et al. |
| 4,563,170 A | 1/1986 | Aigner |
| 4,574,876 A | 3/1986 | Aid |
| 4,576,143 A | 3/1986 | Clark, III |
| 4,602,140 A | 7/1986 | Sobolewski |
| 4,638,135 A | 1/1987 | Aoki |
| 4,678,460 A | 7/1987 | Rosner |
| 4,680,445 A | 7/1987 | Ogawa |
| 4,692,138 A | 9/1987 | Troutner et al. |
| 4,707,587 A | 11/1987 | Greenblatt |
| 4,731,072 A | 3/1988 | Aid |
| 4,759,749 A | 7/1988 | Verkaart |
| 4,782,212 A | 11/1988 | Bakke |
| 4,801,777 A | 1/1989 | Auerbach |
| 4,844,074 A | 7/1989 | Kurucz |
| 4,847,470 A | 7/1989 | Bakke |
| 4,855,552 A | 8/1989 | Marceau et al. |
| 4,874,359 A | 10/1989 | White et al. |
| 4,878,537 A | 11/1989 | Verkaart |
| 4,906,816 A | 3/1990 | van Leerdam |
| 4,907,145 A | 3/1990 | Cassidy |
| 4,908,014 A | 3/1990 | Kroyer |
| 4,938,279 A | 7/1990 | Betker |
| 4,962,761 A | 10/1990 | Golden |
| 5,003,145 A | 3/1991 | Nolle et al. |
| 5,062,775 A | 11/1991 | Orth |
| 5,108,372 A | 4/1992 | Swenson |
| 5,125,069 A | 6/1992 | O'Boyle |
| 5,188,604 A | 2/1993 | Orth |
| 5,245,693 A | 9/1993 | Ford et al. |
| 5,250,032 A | 10/1993 | Carter, Jr. et al. |
| 5,254,094 A | 10/1993 | Starkey et al. |
| 5,319,170 A | 6/1994 | Cassidy |
| 5,344,568 A | 9/1994 | Kitaevich et al. |
| 5,354,277 A | 10/1994 | Guzman et al. |
| 5,381,510 A | 1/1995 | Ford et al. |
| 5,408,577 A | 4/1995 | Weber, Jr. et al. |
| 5,420,962 A | 5/1995 | Bakke |
| 5,476,444 A | 12/1995 | Keeling et al. |
| 5,571,153 A | 11/1996 | Wallsten |
| 5,690,815 A | 11/1997 | Krasnoff et al. |
| 5,702,358 A | 12/1997 | Witherspoon et al. |
| 5,846,224 A | 12/1998 | Sword et al. |
| 5,913,814 A | 6/1999 | Zantos |
| 6,045,648 A | 4/2000 | Palmgren et al. |
| 6,117,076 A | 9/2000 | Cassidy |
| 6,175,688 B1 | 1/2001 | Cassidy et al. |
| 6,236,809 B1 | 5/2001 | Cassidy et al. |
| 6,480,257 B2 | 11/2002 | Cassidy et al. |
| 6,579,496 B1 | 6/2003 | Fausset et al. |
| 6,827,898 B1 | 12/2004 | Fausset et al. |
| 7,819,835 B2 | 10/2010 | Landy et al. |
| 7,842,002 B2 | 11/2010 | Mantle |
| 8,100,881 B2 | 1/2012 | Hoffa |
| 8,387,963 B2 | 3/2013 | Moutafis |
| 8,439,960 B2 | 5/2013 | Burnett et al. |
| 8,480,648 B2 | 7/2013 | Burnett et al. |
| 8,672,884 B2 | 3/2014 | Burnett et al. |
| 8,900,652 B1 | 12/2014 | Caballero et al. |
| 9,737,672 B2 | 8/2017 | Landy et al. |
| 2001/0039441 A1 | 11/2001 | Ash |
| 2003/0139788 A1 | 7/2003 | Eggers et al. |
| 2005/0222653 A1 | 10/2005 | Noda et al. |
| 2006/0089586 A1 | 4/2006 | Kaus et al. |
| 2007/0051409 A1 | 3/2007 | Landy et al. |
| 2009/0012450 A1 | 1/2009 | Shah et al. |
| 2009/0012655 A1 | 1/2009 | Kienman et al. |
| 2009/0043256 A1* | 2/2009 | Landy ............... A61M 5/1407 604/113 |
| 2009/0192446 A1 | 7/2009 | Landy, III et al. |
| 2011/0196302 A1 | 8/2011 | Gildersleeve et al. |
| 2012/0302995 A1 | 11/2012 | Hochareon |
| 2015/0190274 A1 | 7/2015 | Landy et al. |
| 2016/0101228 A1 | 4/2016 | Landy, III et al. |
| 2018/0147368 A1 | 5/2018 | Landy, III et al. |
| 2018/0147370 A1 | 5/2018 | Landy, III et al. |

FOREIGN PATENT DOCUMENTS

| | | |
|---|---|---|
| WO | WO-9640331 A1 | 12/1996 |
| WO | WO-00/02608 A1 | 1/2000 |
| WO | WO-2018/102354 A1 | 6/2018 |

OTHER PUBLICATIONS

Written Opinion, PCT/US2017/063612 (Rapid Infuser With Advantageous Flow Path for Blood and Fluid Warming, and Associated Components, Systems, and Methods, filed Nov. 29, 2017), issued by ISA/US, 9 pages, dated May 9, 2018.

* cited by examiner

SECTION C-C

SECTION D-D

SECTION A-A

DETAIL A

DETAIL A

RAPID INFUSER WITH VACUUM RELEASE VALVE

BACKGROUND

To treat hemorrhaging (e.g., escape of blood from a ruptured vessel), it is often necessary to quickly infuse a substantial volume of fluid, e.g. whole blood, plasma or blood substitute, so as to maintain an adequate blood volume and circulation. However, to preserve blood or blood products, such materials are typically refrigerated, and it is necessary to warm them before infusion so as to avoid shock to a patient's system. While it is desired to heat the infusate quickly, the temperature of the infusate should not exceed 40° C. to 42° C., since at higher temperatures, protein denaturation and red cell damage can occur. It is also important that any electrical power or potentials utilized in the heating process be effectively isolated from a patient.

Furthermore, hyperthermia (e.g., an individual's body temperature elevated above his or her normal range) as a treatment of tumors has been carefully studied and applied. Research has shown that high temperatures can damage cancer cells, usually without significant damage of normal tissues. Temperature and time may be interrelated with respect to tumor necrosis and risk of toxicity to normal cells. With longer time at hyperthermia temperature, more tumor cells, as well as healthy cells may be damaged. Tumor cells may not efficiently dissipate heat due to their disorganized and compact vascular structure; therefore, hyperthermia may cause the tumor cells to undergo apoptosis.

Hyperthermia may be particularly useful for reducing the risk of metastasis by targeting circulating tumor cells within the bloodstream. Cancerous cells may circulate within blood vessels (e.g., after surgical removal, cytoreduction surgery, de-bulking of tumor), attach to 9292473v1 endothelial cells lining the blood vessels, and form secondary tumors or metastatic lesions. However, a targeted treatment may not be possible for those circulating tumor cells. Hyperthermia via body cavities can be effective in treating with circulating tumor cells. While healthy cells (e.g., non-tumor cells) may survive the treatment due to heat transfer to the blood vessels, the floating tumor cells may not.

Fluid warmers often have a sensor connected to inflow tubing to detect if an infusate reservoir is empty. Typically, the sensor comprises a transmitter and a receiver (FIGS. 14A-14C), and measures velocity of ultrasound waves from the transmitter to distinguish between fluid and air, since ultrasound waves travel faster through fluids than air. The inflow tubing is located between the transmitter and the receiver. When the fluid level in the infusate reservoir is low (or zero), the pressure in the infusate reservoir and the inflow tubing can be lower than the atmospheric pressure. Therefore, the non-rigid inflow tubing deforms to minimize the pressure difference. The fluid out sensor measures this deformation.

The direction of deformation affects detectability by the sensor. In some instances, e.g., where the major axis of the elliptical cross-section of the collapsed inflow tubing is parallel to a line between the transmitter and the receiver, the sensor cannot detect the deformation due to lack of air in the ultrasound beam path.

SUMMARY

The present disclosure provides improved technologies relating to a medical fluid heating apparatus. In certain embodiments, the present invention relates to an apparatus for heating a fluid and, more particularly, to an apparatus for quickly and controllably heating flows of blood, or blood product, which may be needed for infusion into a patient, or flows of hyperthermia fluids, to induce tumor necrosis.

The new designs described herein solve problems associated with prior strategies for heating infusate (e.g., blood, hyperthermia flood). In particular, the systems address a system halt failure due to inaccurate detection of fluid level in a reservoir.

Embodiments of the present disclosure include new designs that do not experience undesirable deformation of the inflow tubing which would undermine detectability by a fluid level sensor. In certain embodiments, the new design comprises a vacuum release valve, which supplies air to the inflow tubing allowing fluid out detection caused by the presence of air. The supplied air reduces the pressure difference between the inflow tubing and the atmosphere, thereby preventing the deformation of the inflow tubing and avoiding a possible failure to activate a system halt.

In one aspect, the invention directed to a system for heating a fluid, which comprises a conduit (e.g., toroid-shaped) defining a central opening, a primary inductor at least partially within the central opening, one or more secondary inductors within the conduit (e.g., wherein each of the one or more secondary inductors is ring-shaped, flat), the conduit defining a central opening, an inflow tubing connected to the conduit, and a vacuum release valve. In certain embodiments, each of the one or more secondary inductors is substantially parallel. In certain embodiments, the secondary inductors are separated by gaps (or spaces). In certain embodiments, the primary inductor comprises a coil (or a winding). In certain embodiments, when the primary inductor is energized, the coil generates magnetic flux passing through the central opening. In certain embodiments, when pressure in the inflow tubing is lower than atmospheric pressure, the vacuum release valve allows flow of air into the inflow tubing, thereby rapidly allowing the detection of a fluid out condition.

In certain embodiments, the system further comprises a reservoir for containing an infusate. In certain embodiments, the vacuum release valve is connected to the reservoir. In certain embodiments, the vacuum release valve is connected to the top of the reservoir. In certain embodiments, the vacuum release valve is connected to the bottom of the reservoir. In certain embodiments, the reservoir further comprises a tubing attached to the top of the reservoir, and the vacuum release valve is connected to the reservoir through the tubing.

In certain embodiments, the vacuum release valve allows flow of air into the inflow tubing when pressure in the inflow tubing is 1, 2, 3, 4, 5, 6, 7, 8, 9, or 10 psi lower than atmospheric pressure.

In certain embodiments, the conduit provides a single fluid flow path. In certain embodiments, the single fluid flow path has a conformation such that fluid is not in contact with the primary inductor.

In certain embodiments, the system further comprises a fluid separator comprising an inlet nozzle and an outlet nozzle, wherein the inlet nozzle directs an inlet flow to the conduit through the fluid separator and the outlet nozzle receives an outlet flow from the conduit through the fluid separator.

In certain embodiments, the conduit comprises a plurality of spacers which provides the gaps between the secondary inductors.

In certain embodiments, wherein the one or more secondary inductors transfers heat to fluid within the conduit.

In certain embodiments, the system further comprises a bubble trap for removing air bubbles from fluid flowing through the system.

In another aspect, the invention directed to a disposable unit of a system for heating a fluid, which comprises a conduit (e.g., toroid-shaped) defining a central opening, one or more secondary inductors within the conduit (e.g., wherein each of the one or more secondary inductors is ring-shaped, flat), an inflow tubing connected to the conduit, and a vacuum release valve. In certain embodiments, each of the one or more secondary inductors is substantially parallel.

In certain embodiments, the disposable unit further comprises a reservoir for containing an infusate. In certain embodiments, the vacuum release valve is connected to the reservoir. In certain embodiments, the vacuum release valve is connected to the top of the reservoir. In certain embodiments, the vacuum release valve is connected to the bottom of the reservoir. In certain embodiments, the reservoir further comprises a tubing attached to the top of the reservoir, and the vacuum release valve is connected to the reservoir through the tubing.

In certain embodiments, the disposable unit comprises a fluid separator comprising an inlet nozzle and an outlet nozzle. In certain embodiments, the conduit defines a single fluid flow path. In certain embodiments, the disposable unit further comprises a bubble trap for removing air bubbles from fluid flowing through the system.

A more complete understanding of the invention, as well as further features and advantages thereof, will be obtained by reference to the following detailed description read in conjunction with the accompanying drawings.

BRIEF DESCRIPTION OF THE DRAWINGS

The Drawings, which are comprised of at least the following Figures, are for illustration purposes only, not for limitation.

The foregoing and other objects, aspects, features, and advantages of the present disclosure may become more apparent and better understood by referring to the following description taken in conduction with the accompanying drawings, in which.

DEFINITIONS

Figure 1:
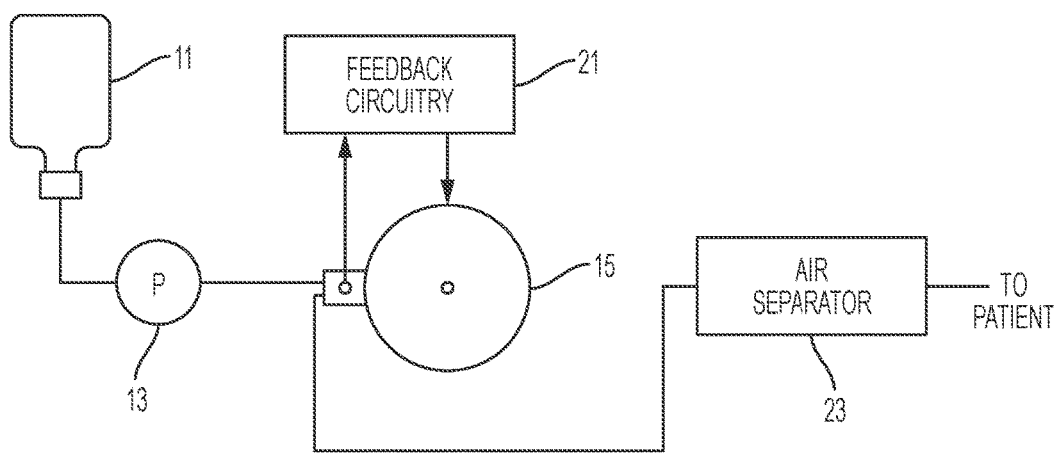
FIG. 1 is a schematic block diagram of a fluid heating apparatus, according to an illustrative embodiment of the present invention.

In order for the present disclosure to be more readily understood, certain terms are first defined below. Additional definitions for the following terms and other terms are set forth throughout the specification.

As used herein, the term "administration" typically refers to the administration of a composition to a subject or system. Those of ordinary skill in the art will be aware of a variety of routes that may, in appropriate circumstances, be utilized for administration to a subject, for example a human. For example, in certain embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In certain embodiments, administration may involve dosing that is intermittent (e.g., a plurality of doses separated in time) and/or periodic (e.g., individual doses separated by a common period of time) dosing. In certain embodiments, administration may involve continuous dosing (e.g., perfusion) for at least a selected period of time.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, the term "designed" refers to an agent (i) whose structure is or was selected by the hand of man; (ii) that is produced by a process requiring the hand of man; and/or (iii) that is distinct from natural substances and other known agents.

As used herein, the term "low flow rate" refers to a non-zero (e.g., no less than 1 ml/min) flow rate less than about 100 ml/min, or less than about 50 ml/min, or less than about 40 ml/min, or less than about 30 ml/min, or less than about 20 ml/min, or less than about 15 ml/min, or less than about 10 ml/min.

As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In certain embodiments, a patient is a human. In certain embodiments, a patient is suffering from or susceptible to one or more disorders or conditions. In certain embodiments, a patient displays one or more symptoms of a disorder or condition. In certain embodiments, a patient has been diagnosed with one or more disorders or conditions. In certain embodiments, the disorder or condition is or includes cancer, or presence of one or more tumors. In certain embodiments, the patient is receiving or has received certain therapy to diagnose and/or to treat a disease, disorder, or condition.

As used herein, the term "substantially" refers to the qualitative condition of exhibiting total or near-total extent or degree of a characteristic or property of interest.

As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In certain embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the claims presented herein. The Background section is presented for purposes of clarity and is not meant as a description of prior art with respect to any claim.

As mentioned above, the present disclosure relates to warming of fluid (e.g., blood, blood products, hyperthermia fluid, and more). The present disclosure encompasses system, apparatus and/or methods of warming fluids.

Most rapid fluid warmers utilize a relatively large water bath reservoir which is preheated to 39 to 40° C. Water is pumped rapidly through a heat exchanger through which the infusate is perfused, the two fluids typically being separated by a thin, usually metallic, heat exchange surface. These devices are relatively large and cumbersome due to the need for the water bath and water pump, as well as a heat exchanger and associated conduits. Such devices accordingly are not ideal for use in emergency situations.

Other rapid fluid warmers utilize resistive heating (i.e., Joule heating) to increase temperature of the infusate. The resistive heaters are smaller than the heaters with the water bath, however, the resistive heaters can encounter overheating the infusate. A local temperature of the resistive heaters can reach up to about 80° C., denaturing proteins in the infusate.

Commercially available rapid fluid warmers are described in, for example, U.S. Pat. Nos. 5,319,170, 6,175,688, 6,236,809, 6,480,257, and 7,819,835.

Some blood warmers (e.g., the Belmont® Rapid Infuser, the Belmont® Hyperthermia Pump) utilize inductive or electro-magnetic heating techniques, involving a circular heat exchanger tailored to the shape of the magnetic field. Fluid is introduced into the toroid at a point where the fluid path bifurcates with each half flowing on opposites sides of the toroid, until the two halves rejoin at the fluid output of the toroid. The electro-magnetic heater includes a primary inductor (coil), generating an alternating magnetic field. A high current density in the secondary inductor converts electric energy into thermal energy, so that the secondary inductor provides heat to a fluid. This effective heat exchange system of the Belmont® Rapid Infuser enables fluid (e.g., blood, blood products with temperature of 4 to 37.5° C.) to be heated to a target temperature (e.g., normothermia) in a single pass. Moreover, a user can control heat flux to the fluid precisely, thus, the electro-magnetic heating system prevents overheating. Furthermore, size of the Belmont® Rapid Infuser and the Belmont® Hyperthermia Pump is significantly smaller (e.g., IV-pole mountable) than other commercial fluid heaters.

Embodiments described herein address a problem that can sometimes arise with toroidal heat exchangers with dual flow paths. At low flow rates, the pressure drop from the flow paths to the outlet may be insufficient to support flow through both paths, causing flow to occur on a single side of the dual flow path, only. The other side of the dual flow path, therefore, encounters stagnant or slow flow. The stagnant or slow flow in a toroidal heat exchanger may be a concern, when blood or blood products have either been improperly anticoagulated or have had the anticoagulant compromised (e.g., mixed with lactated Ringer's or other solution containing calcium), clogs may occur. For example, if the blood or blood product coagulate in one of the flow paths which has stagnant or slow flow, that flow path can become clogged. When the system with the clogged flow path starts to supply heated fluids at a sufficiently high rate (e.g., with an increased heat supply to the heat exchangers), the clogged flow path can become overheated due to insufficient supply of fluids, which absorb heat from the heat exchangers (e.g., decrease the temperature of the heat exchangers).

Embodiments of the present disclosure include new designs that provide a single flow path without compromising advantages of the existing blood warmers, such that the heat exchanger would not experience stagnant flow that may cause overheating of a local flow path. The single flow path is found to obviate problems that may occur with the dual flow path system due to improper usage (e.g., use of blood or blood products that have not been properly anticoagulated).

Fluid Heating System

Figure 2:
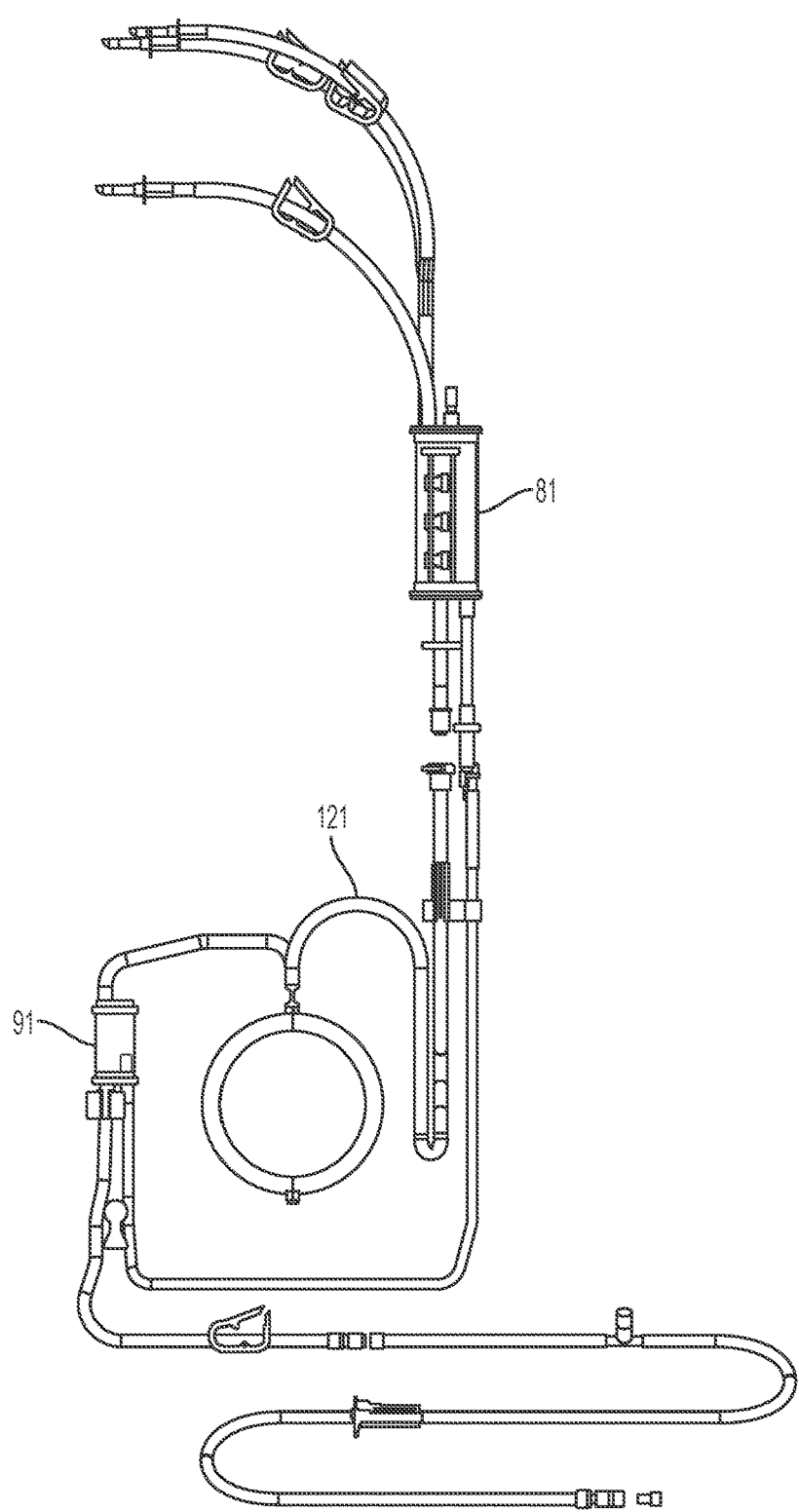
FIG. 2 is a front view of a disposable set, according to an embodiment of the instant invention.

In certain embodiments, as illustrated in FIGS. 1 and 2, a fluid heating system comprises a reservoir of infusate (e.g., blood, plasma or other solution). Fluid tubular lines and connectors of an infusion fluid disposable set, for example, as described in FIG. 2, direct fluid to reservoirs of the infusion fluid disposable set. Additional tubular fluid lines and connectors of a disposable set direct fluid from reservoirs to and through a heater. Infusate drawn from reservoir 11 is driven by a pump 13 (e.g., roller pump) through an inductive heater constructed in accordance with the present disclosure. Heated fluid is directed into a patient tubular fluid feed line to a patient's body.

In heater 15, infusate is brought to a preselected temperature; control of the temperature is affected by feedback circuitry 21 and responds to outlet temperature, e.g., as sensed by a temperature sensor 51 to control the energization of an inductor, which effects the heat generation in the heater 15. This feedback circuitry is described in greater detail below. From the heater 15, the infusate passes through a separator 23, which removes all air and then passes to the patient.

Figure 3:
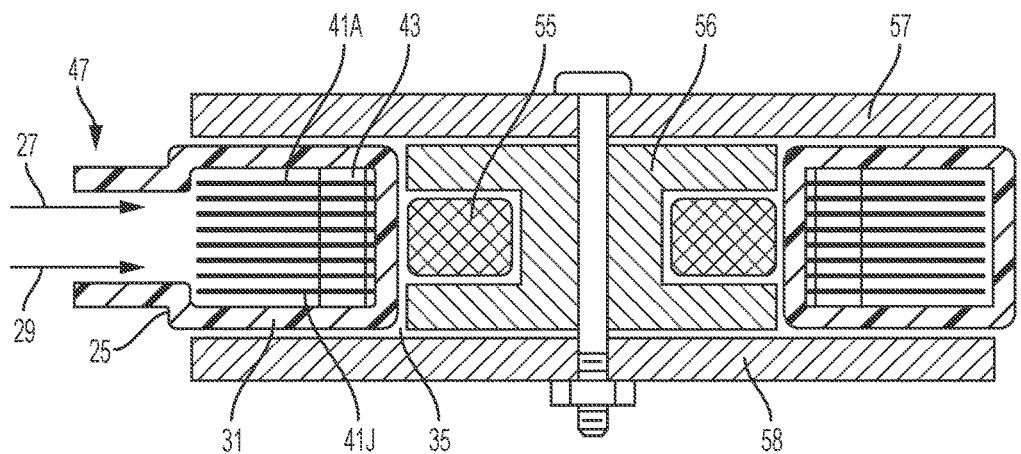
FIG. 3 is a cross-sectional view of an inductive heater employed, shown with a primary inductor, secondary inductors, a conduit, an inlet and an outlet, according to an illustrative embodiment of the present invention.
Figure 4:
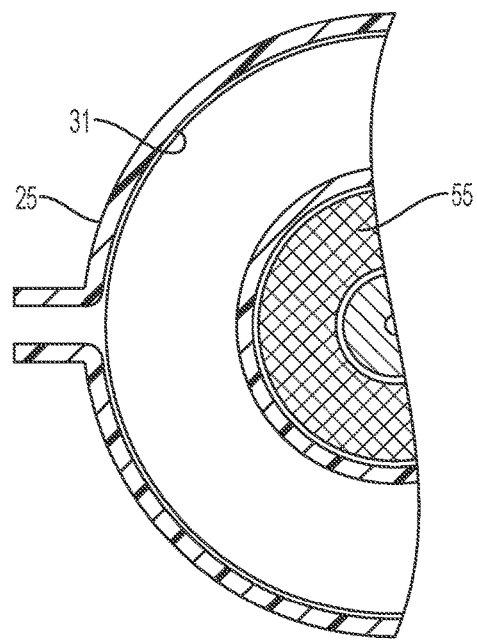
FIG. 4 is a plan view, with parts broken away, of the heater of FIG. 3.
Figure 5:
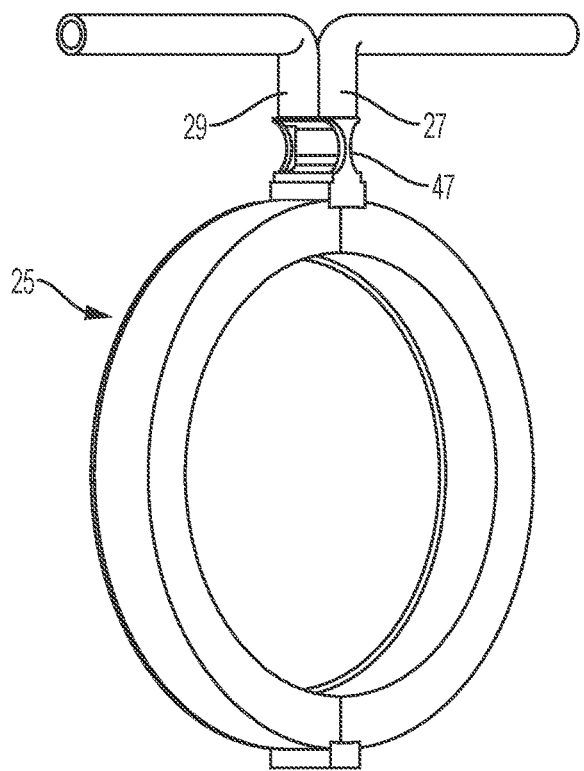
FIG. 5 illustrates a single flow path conduit with a fluid separator comprising an inlet nozzle and an outlet nozzle, according to an embodiment of the present invention.

In certain embodiments, as is illustrated in greater detail in FIGS. 3 and 4, the heater 15 involves a conduit or housing 25, which may be constructed of a suitable plastic material. A fluid separator 47 provides an inlet 27 and an outlet 29, which are connected by a ring-like annular chamber 31, which defines a single flow path with an opening 35. While the exemplary path is shown as forming a circle, it should be understood that other shapes could also be used, e.g. ovoid.

A primary inductor comprising a winding 55 wound on a ferrite bobbin core 56 generates magnetic flux passing through the central opening andis inductively coupled to a plurality of secondary inductors 41A-41J for inducing local currents therein. The winding, however, does not surround the flow path. To improve the degree of coupling between the winding 55 and the secondary inductors 41A-41J, ferrite magnetic end plates 57 and 58 may be employed to extend the flux coverage.

Heat Exchanger

In certain embodiments, as illustrated in FIGS. 1 and 2, a fluid heating system comprises a reservoir of infusate (e.g., blood, plasma or other solution). Fluid tubular lines and connectors of an infusion fluid disposable set, for example, as described in FIG. 2, direct fluid to reservoirs of the infusion fluid disposable set. Additional tubular fluid lines and connectors of a disposable set direct fluid from reservoirs to and through a heater. Infusate drawn from reservoir 11 is driven by a pump 13 (e.g., roller pump) through an inductive heater constructed in accordance with the present disclosure. Heated fluid is directed into a patient tubular fluid feed line to a patient's body.

In heater 15, infusate is brought to a preselected temperature; control of the temperature is affected by feedback circuitry 21 and responds to outlet temperature, e.g., as sensed by a temperature sensor 51 to control the energization of an inductor, which effects the heat generation in the heater 15. This feedback circuitry is described in greater detail below. From the heater 15, the infusate passes through a separator 23, which removes all air and then passes to the patient.

In certain embodiments, as is illustrated in greater detail in FIGS. 3 and 4, the heater 15 involves a conduit or housing 25, which may be constructed of a suitable plastic material. A fluid separator 47 provides an inlet 27 and an outlet 29, which are connected by a ring-like annular chamber 31, which defines a single flow path with an opening 35. While the exemplary path is shown as forming a circle, it should be understood that other shapes could also be used, e.g. ovoid.

A primary inductor comprising a winding 55 wound on a ferrite bobbin core 56 generates magnetic flux passing through the central opening and is inductively coupled to a plurality of secondary inductors 41A-41J for inducing local currents therein. The winding, however, does not surround the flow path. To improve the degree of coupling between the winding 55 and the secondary inductors 41A-41J, ferrite magnetic end plates 57 and 58 may be employed to extend the flux coverage.

Heat Exchanger

In certain embodiments, the heat exchanger comprises thin or ribbon-like secondary inductors 41A-41J) contained in a chamber 31. As illustrated, the secondary inductors have a circular ring-like shape. In alternative embodiments, other shapes (e.g., beads) can be used. In certain embodiments, the secondary inductors extend generally parallel to each other in a spaced relationship (spaced apart) with each secondary inductor passing through the flow path so as to heat the fluid. As will be apparent, fluid flowing from the inlet 27 to outlet 29 will pass through the spaces between the secondary inductors 41A-41J and will be in intimate thermal contact therewith.

In certain embodiments, the chamber 31 is circular and the secondary inductors 41A-41J are correspondingly formed as flat rings. This shape simplifies obtaining symmetry and uniform heating. In other embodiments, other shapes are used. Spacing between adjacent secondary inductors 41A-41J is maintained by spacers 43.

In certain embodiments, where amounts and/or properties of the fluids in the heating system change, it is desirable to modify certain key parameters of the heat exchanger. When a fluid is in contact with a solid surface, heat flux between the fluid and the solid surface, the rate of heat energy transfers through the given surface per unit time, can be expressed as follows:

$$q = h \cdot \Delta T$$

wherein q is heat flux (W/m$^2$), h is a heat transfer coefficient (W/m$^2$·K), and $\Delta T$ is the difference in temperature between the solid surface and surrounding fluid area (K). The heat transfer coefficient is a function of the key parameters, for example, conductivity of the solid (e.g., the secondary inductors), gaps between the secondary inductors, etc. Total heat transfer from the solid surface to the fluid can be calculated by multiplying total surface area to heat flux. Therefore, when one changes fluid to be heated and/or operating conditions, it may be desirable to increase or decrease gaps between the secondary inductors, increase or decrease the number of secondary conductors, change the total surface area of secondary inductors, and/or change materials used in the construction of the secondary inductors. For example, in order to accommodate a higher heating capacity (e.g., higher flow rate), the number and/or the total surface area of the secondary conductors may be increased.

In certain embodiments, the secondary inductors is constructed, for example, of stainless steel. Other conductive materials such as conductive plastics might also be used. In certain embodiments, one or more conductive materials are selected from the group consisting of stainless steel, carbon (graphene), silver, copper, gold, aluminum, tungsten, zinc, nickel, lithium, iron, platinum, tin, carbon steel, lead, titanium, grain oriented electrical steel, manganin, constantan, mercury, nichrome, carbon (graphite) and combinations thereof. In certain embodiments, one chooses less conductive material (e.g., high resistance) to generate increased dissipation heat in the secondary inductors.

In certain embodiments, a conduit/chamber of the present disclosure has at least 1, 2, 4, 6, 8, 10, 12, 14, 16, 18 or 20 secondary inductors.

In certain embodiments, each gap between secondary inductors has a distance of about 0.001" to about 0.1", about 0.001" to about 0.1", about 0.001" to about 0.1", or about 0.02" to about 0.03".

In certain embodiments, total surface area of secondary inductors is about 1 to about 1000 in$^2$, about 1 to about 500 in$^2$, about 1 to about 250 in$^2$, about 10 to about 1000 in$^2$, about 10 to about 500 in$^2$, or about 10 to about 250 in$^2$.

Fluid Separator

In certain embodiments, a fluid separator is incorporated into a single flow path heating system. The fluid separator may enable a single flow path with minimal modification of the existing system (e.g., same the primary inductor, tubing, etc.). An exemplary fluid separator is depicted in FIGS. 6A-6G, 7A, 7B and 8. The fluid separator comprises an inlet nozzle and an outlet nozzle. The inlet nozzle 27 directs unheated (e.g., cold) fluid to the single flow path, while the outlet nozzle 29 receives heated fluid from the single flow path. The inlet and outlet nozzle are substantially parallel to each other to allow flow through the outlet nozzle in an opposite direction to flow through the inlet nozzle.

In certain embodiments, the fluid separator has a housing. The housing provides an inlet chamber and an outlet chamber in the fluid separator. The inlet (e.g., unheated) fluid first enters into the inlet chamber, and then moves into the single fluid path. The outlet (e.g., heated) fluid exits from the single fluid path, then passes through the outlet chamber. Temperatures of the inlet fluid and outlet fluid can be measured at exterior walls of the inlet chamber and the outlet chamber, respectively. A portion of the housing is sufficiently thermally-conductive, so that the temperature of the fluid (e.g., inlet unheated fluid, outlet heated fluid) is substantially identical to the temperature of the housing (e.g., outside of the inlet chamber, the outlet chamber) in contact with the fluid. In certain embodiments, the housing comprise a notch that can secure a divider. In certain embodiments, the housing has two convex walls at the inlet chambers and the outlet chambers, from the perspective of each of the inlet chamber and the outlet chamber as shown in FIGS. 6E and 6G. Temperature probes may measure inlet and outlet temperatures at the convex walls.

In certain embodiments, a fluid separator comprises a divider separating the unheated fluid in the inlet chamber and the heated fluid in the outlet chamber. The inlet nozzle 27 and the outlet nozzle 29 are connected to different sections of the fluid separator, so that the divider effectively separates the unheated fluid and the heated fluid.

The divider 48 may have a solid upper portion 48A to satisfactorily separate the inlet chamber from the outlet chamber when the divider is secured in the fluid separator. The divider 48 may also have a lower portion comprising a plurality of elongations 49 to accommodate a plurality of secondary inductors. For example, each elongation 49 may block each gap between the ring shaped secondary inductors 41A-41P, so that the divider prevents mixing of the unheated fluid and the heated fluid between the secondary inductors. In certain embodiments, each thickness of the elongations 49 are substantially identical to each gap between the secondary inductors. In certain embodiments, the width of the notch and the thickness of the divider are substantially identical, so that the notch can secure the divider in the fluid separator.

Figure 6A:
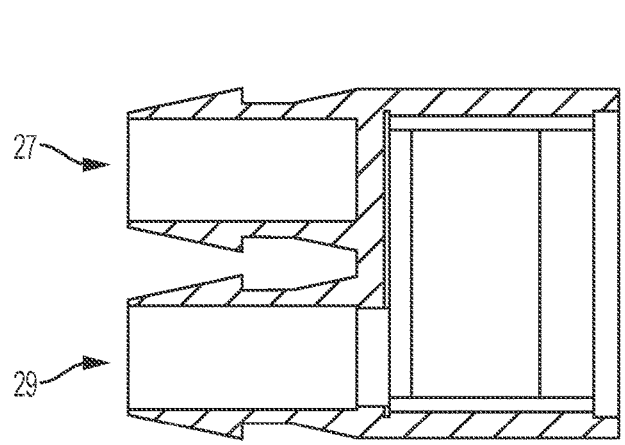
FIGS. 6A-6G illustrate a fluid separator, according to an embodiment of the present invention.
Figure 6B:
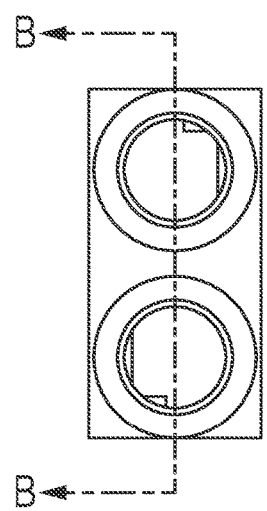
Figure 6C:
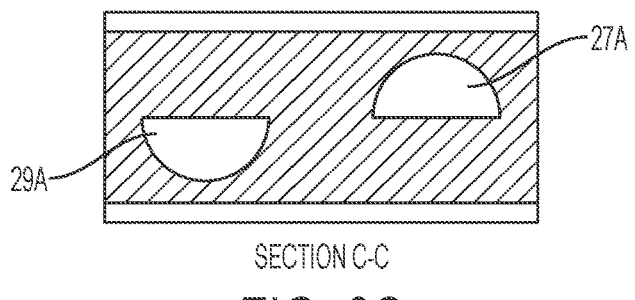
Figure 6D:
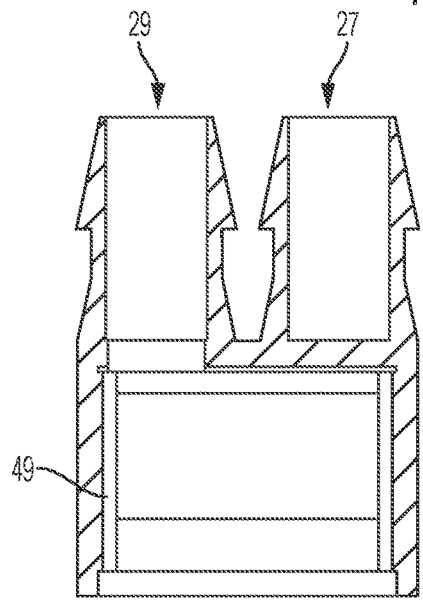
Figure 6E:
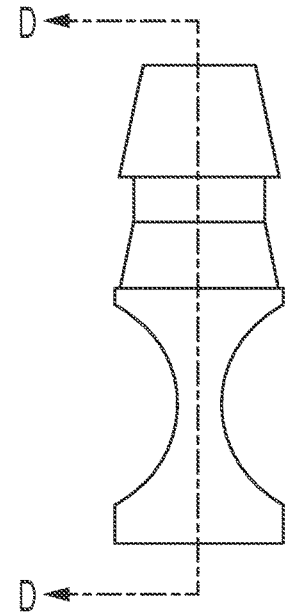
Figure 6F:
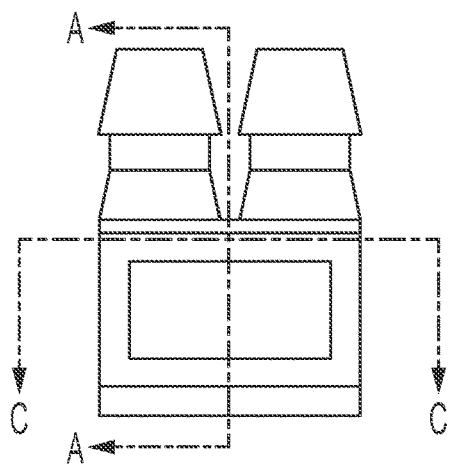
Figure 6G:
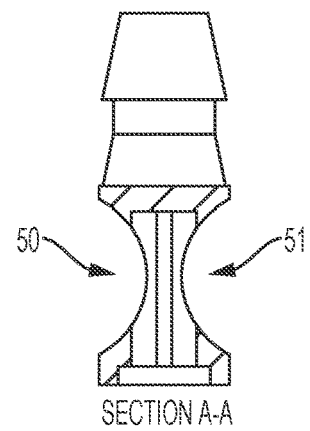
Figure 7A:
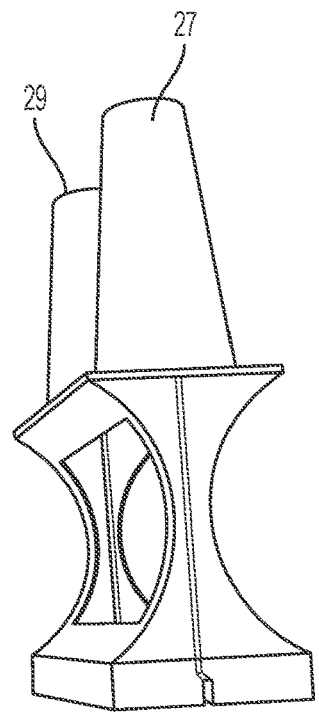
FIGS. 7A and 7B are optical images of a fluid separator, according to an embodiment of the present invention.
Figure 7B:
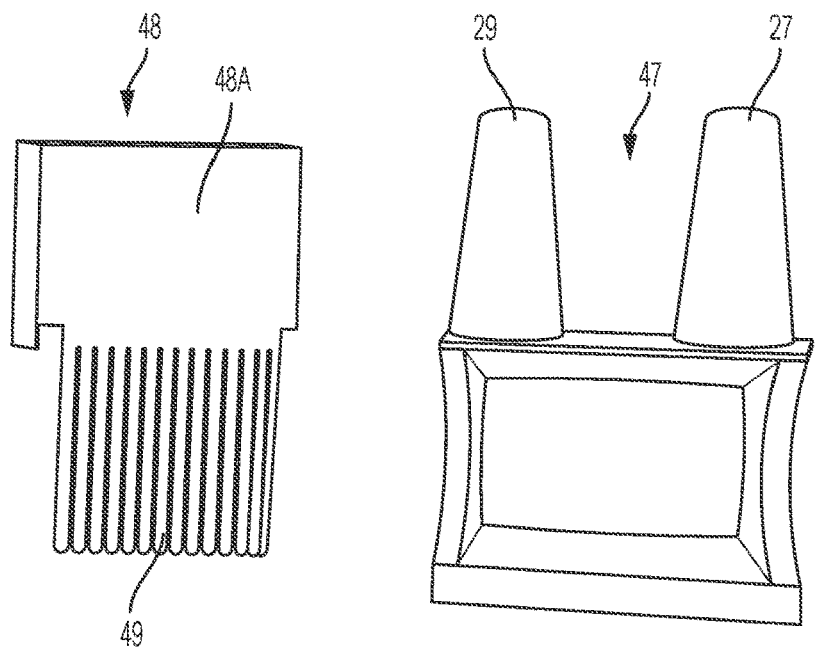

In certain embodiments, the cross section of the inlet nozzle 27A, where it is connected to the inlet chamber is semi-circular as shown in FIG. 6C. Similarly, the cross section of the outlet nozzle 29A, where it is connected to the outlet chamber may be semi-circular. The semi-circular cross-sections of the inlet and the outlet are located on opposite sides of the fluid divider, so that the divider can separate the inlet and the outlet when the divider is positioned therebetween.

Figure 8:
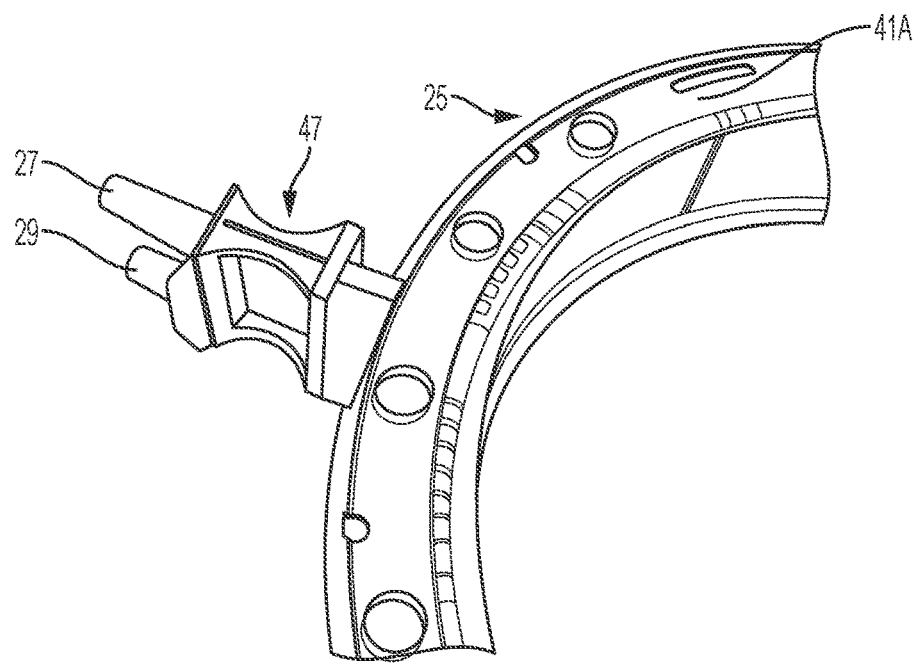
FIG. 8 shows a part of a disposable set with a fluid separator, a conduit and a plurality of secondary inductors, according to an embodiment of the present invention.
Figure 9A:
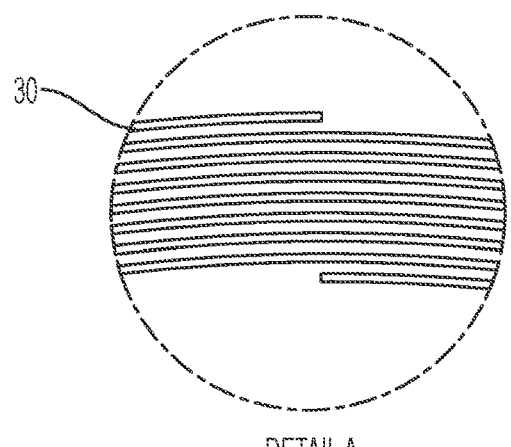
FIGS. 9A-9E depict a spiral inductive tube, according to an embodiment of the present invention.
Figure 9B:
Figure 9C:
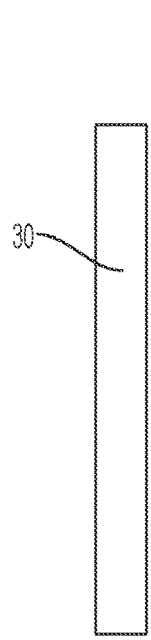
Figure 9D:
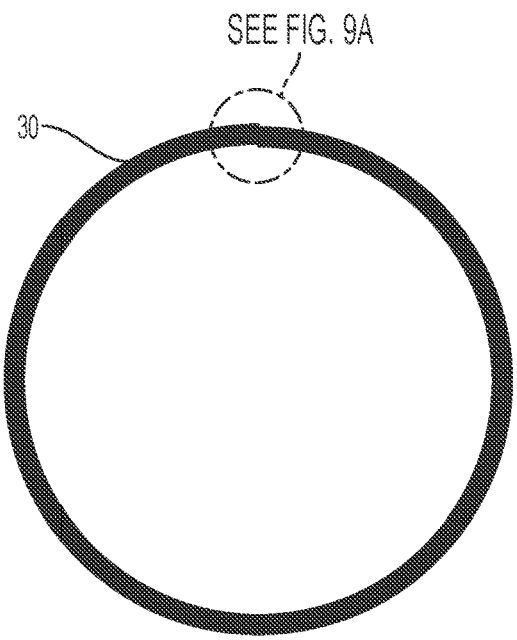
Figure 9E:
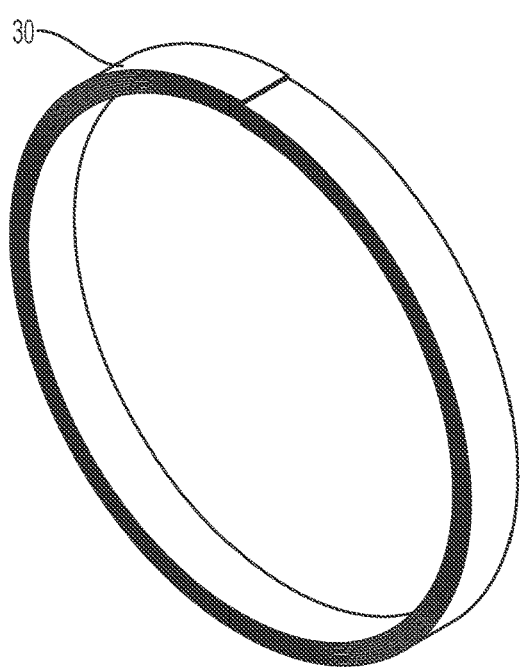
Figure 10A:
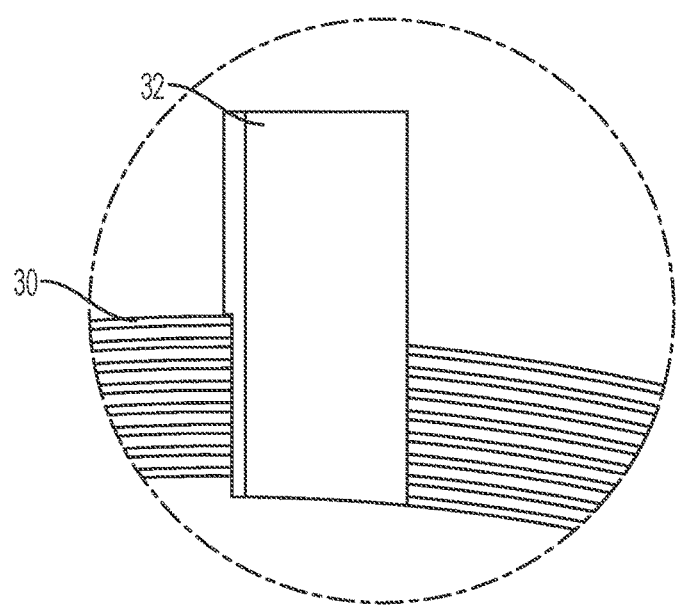
FIGS. 10A-10E depict a spiral inductive tube, according to other embodiments of the present invention.
Figure 10B:
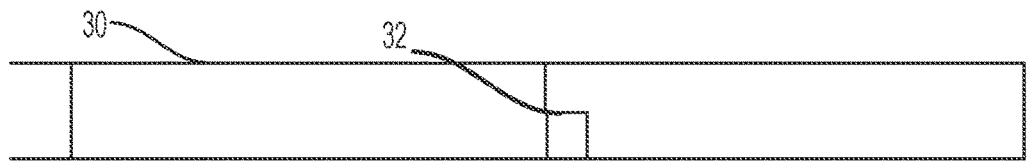
Figure 10C:
Figure 10D:
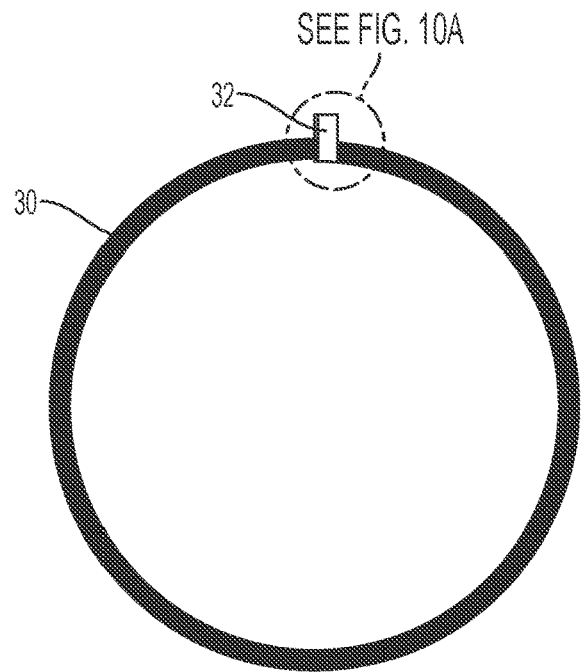
Figure 10E:
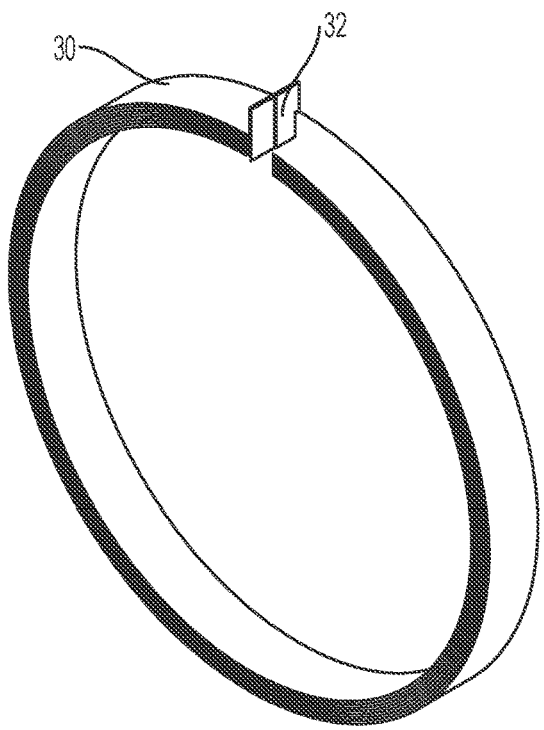

In certain embodiments, the fluid separator is connected to the peripheral area of the conduit, as shown in FIG. 8, so that the inlet nozzle and the outlet nozzle do not disturb alternating magnetic fields created by the primary inductor.

In certain embodiments, seams between the divider and the housing are sealed. In certain embodiments, seams between the elongations of the divider and the secondary inductors may be sealed. Adhesive may be applied at seams and cured with ultraviolet light.

In certain embodiments, a fluid separator of the present disclosure is constructed of insulating materials, for example, polymers and/or plastic so that the separator does not disturb the magnetic field in any instance.

Spiral Inductive Tube

In certain embodiments, a spiral inductive tube provides a single flow path (e.g., instead of a fluid separator, a conduit, and secondary inductors). Exemplary spiral inductive tubes are depicted in FIGS. 9A-9E and 10A-10E. A tube (e.g., conductive tube) may be shaped into a circular form, creating the spiral inductive tube. The spiral tube comprises one or more circular loops. The spiral tube may comprise one or two extended tails, which can be connected to an inlet and/or outlet. The spiral tube may comprise a window for measuring temperature of the fluid flowing.

Similar to embodiments with thin ring-shaped secondary inductors, a primary inductor may be inserted into a central opening of the spiral inductive tube, inductively coupling to the spiral inductive tube for generating local currents therein. An unheated fluid enters and flows within the spiral inductive tube, contacting the inner walls of the spiral inductive tube. Heat generated within the inductive walls of the spiral inductive tube (e.g., due to the alternating magnetic fields from the primary inductor) is transferred to the fluid in the spiral inductive tube.

In certain embodiments, the spiral inductive tube comprises one or more conductive wires (e.g., copper) that electrically connect loops. The conductive wires further provide electrical shorts within the spiral inductive tube.

In certain embodiments, the spiral inductive tube comprises an insulating housing (e.g., polymer, plastic).

In certain embodiments, where amounts and/or properties of the fluids in the heating system, it may be desirable to modify certain key parameters of the spiral inductive tube. For example, it is desirable to increase or decrease inner and/or outer diameters of the spiral inductive tube, increase or decrease the number of windings, change the total surface area of the spiral inductive tube, and/or change materials used in the construction of the spiral inductive tube. For example, in order to accommodate a higher heating capacity, the total surface area and/or winding of the secondary conductors may be increased.

In certain embodiments, a spiral inductive tube is constructed of one or more conductive materials selected from the group consisting of stainless steel, carbon (graphene), silver, copper, gold, aluminum, tungsten, zinc, nickel, lithium, iron, platinum, tin, carbon steel, lead, titanium, grain oriented electrical steel, manganin, constantan, mercury, nichrome, carbon (graphite) and combinations thereof.

In certain embodiments, a spiral inductive tube has a total interior surface area of about 1 in$^2$ to about 1000 in$^2$, about 5 in$^2$ to about 1000 in$^2$, about 10 in$^2$ to about 1000 in$^2$, about 1 in$^2$ to about 500 in$^2$, about 1 in$^2$ to about 100 in$^2$, or about 1 in$^2$ to about 50 in$^2$.

In certain embodiments, an inner diameter of a spiral inductive tube ranges from about 1/32" to about 1", from about 1/16" to about 1", from about 1/32" to about 1/2", from about 1/32" to about 1/4", or from about 1/16" to about 1/4".

In certain embodiments, a spiral inductive tube winds about 1 to about 20 times, about 1 to about 10 times, or about 1 to about 5 times.

Operation

Figure 13:
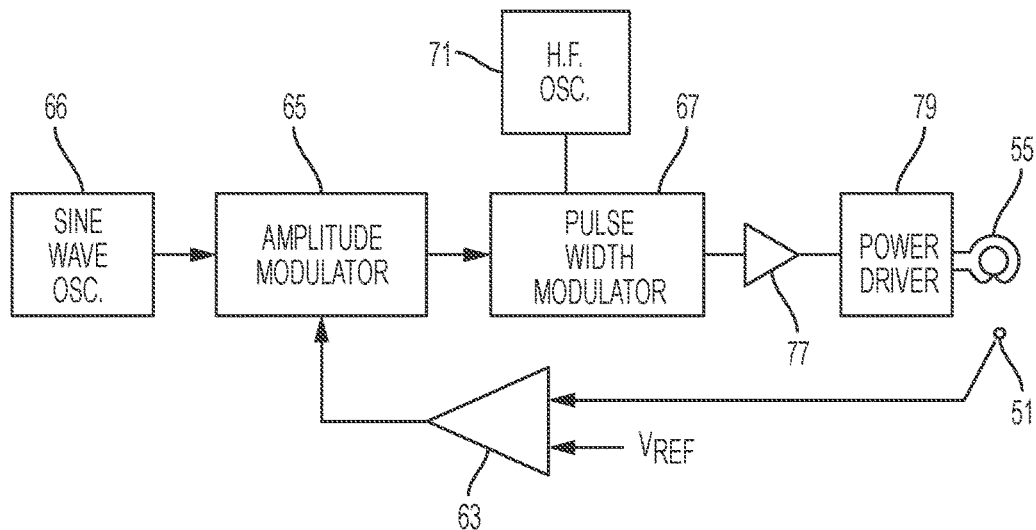
FIG. 13 is a schematic block diagram of circuitry for energizing the inductive heater of FIGS. 3 and 4.

As indicated previously, the energy inductively coupled to the secondary inductors 41A-41J or the spiral inductive tube is preferably controlled to maintain a preselected temperature at the outlet of the heater. Circuitry suitable for this purpose is illustrated in FIG. 13. The sensor 51 provides an output signal corresponding to the temperature at the outlet of the heater. This temperature signal is compared with a reference voltage representing a desired temperature, e.g. 42° C., by an error amplifier designated generally by reference character 63.

The error signal obtained from the error amplifier 63 is applied to a modulator 65 which modulates an amplitude cycle of a low frequency signal obtained from a sine wave oscillator 66. The pulse width of this amplitude modulated signal is in turn varied, as indicated at 67 using a high frequency signal obtained from an oscillator 71. This results in a signal or waveform having a high frequency carrier, but with an energy content proportional to its low frequency amplitude. This signal is in turn applied through suitable driver circuitry 77 to a bridge type power output circuit 79, which provides alternating current energization of the inductor winding 55.

As will be understood by those skilled in the art, power transferred to the secondary inductors 41A-41J or the spiral inductive tube will be determined essentially by the average power content of the waveform applied to the winding 55, thus, this power will be modulated in accordance with an error signal such that the temperature at the output of a heater is maintained at a value substantially equal to the desired or set point temperature. Further, since the heat is generated in the secondary inductors 41A-41J or the spiral inductive tube themselves which are in intimate thermal contact with the fluid passing through the heater, a very high overall efficiency is obtained. Further, since the volume of fluid within the heater at any given moment is relatively small as compared with other devices, a relatively quick response is obtained and very little fluid is lost or unavailable to a patient, since the volume required to fill the system is correspondingly small.

In certain embodiments, an exemplary system of the present disclosure receives electric power by an Alternating Current (AC) wall outlet. In certain embodiments, the system is operated from battery power.

In certain embodiments, the system offers adjustability of flow rate of a fluid from 1 ml/min to 2000 ml/min, or from 10 ml/min to 2000 ml/min. As discussed herein, the system obviates clogging problems that may result from low flow in dual flow path systems. Thus, the embodiments of the single flow path system described herein provide for advantageous operation at low flow rates, e.g., non-zero flow rates of less than about 100 ml/min, or less than about 50 ml/min, or less than about 40 ml/min, or less than about 30 ml/min, or less than about 20 ml/min, or less than about 15 ml/min, or less than about 10 ml/min.

In certain embodiments, an exemplary system of the present disclosure comprises a bubble trap that separates air from fluid by gravitational force. For example, the bubble trap may have a chamber. Air introduced by a pump into a fluid may move to the top of the chamber, while the heated fluid exits from the bottom of the chamber.

Some part of the system needs to be disposable or replaceable from use to use. All of the electronics, energizing inductor and magnetic cores can be used repeatedly. In certain embodiments, a conduit is included as part of a disposable set. In certain embodiments, secondary inductors are included as part of a disposable set. In certain embodiments, a fluid separator is included as part of a disposable set. In certain embodiments, a spiral inductive tube is included as part of a disposable set. In certain embodiments, a bubble trap is included as part of a disposable set. In certain embodiments, a housing is included as part of a disposable set. In certain embodiments, a disposable set is for a single use. A disposable set is constructed of materials that can be sterilized and made pyrogen free by conventional methods and so that single uses thereof are economically feasible.

In certain embodiments, components that the biological fluid (e.g., blood) contacts are biocompatible and/or sterilizable or replaceable.

Slack Time Heating System

Administration of cold blood and other fluids at high flow rates (e.g., greater than 500 ml/min, or greater than 750 ml per minute) using an in line warming system requires the delivery of high quantities of power to the fluids. To infuse cold fluids at a rate in excess of these levels would require more energy than the typical AC outlet can supply. Certain systems store thermal energy in a separate fluid (e.g., water or oil, not infusate) for transferring the stored heat from the fluid to the infusate during times of need. Drawbacks of this approach include the necessity to later transfer energy to the infusate before/during infusion with the limited heat transfer rate of the system (e.g., due to a limited surface area between water/oil and infusate) and the potential contamination of the infusate by the fluid bath.

The present disclosure is directed to a slack-time heating system that utilizes excess heating capacity of fluid heaters to pre-warm fluid in a reservoir. The present disclosure describes a heating system to store heat energy within a reservoir (e.g., in infusate) during off peak periods (e.g., when low flow is required) for later use (e.g., when high flow is required).

Figure 12:
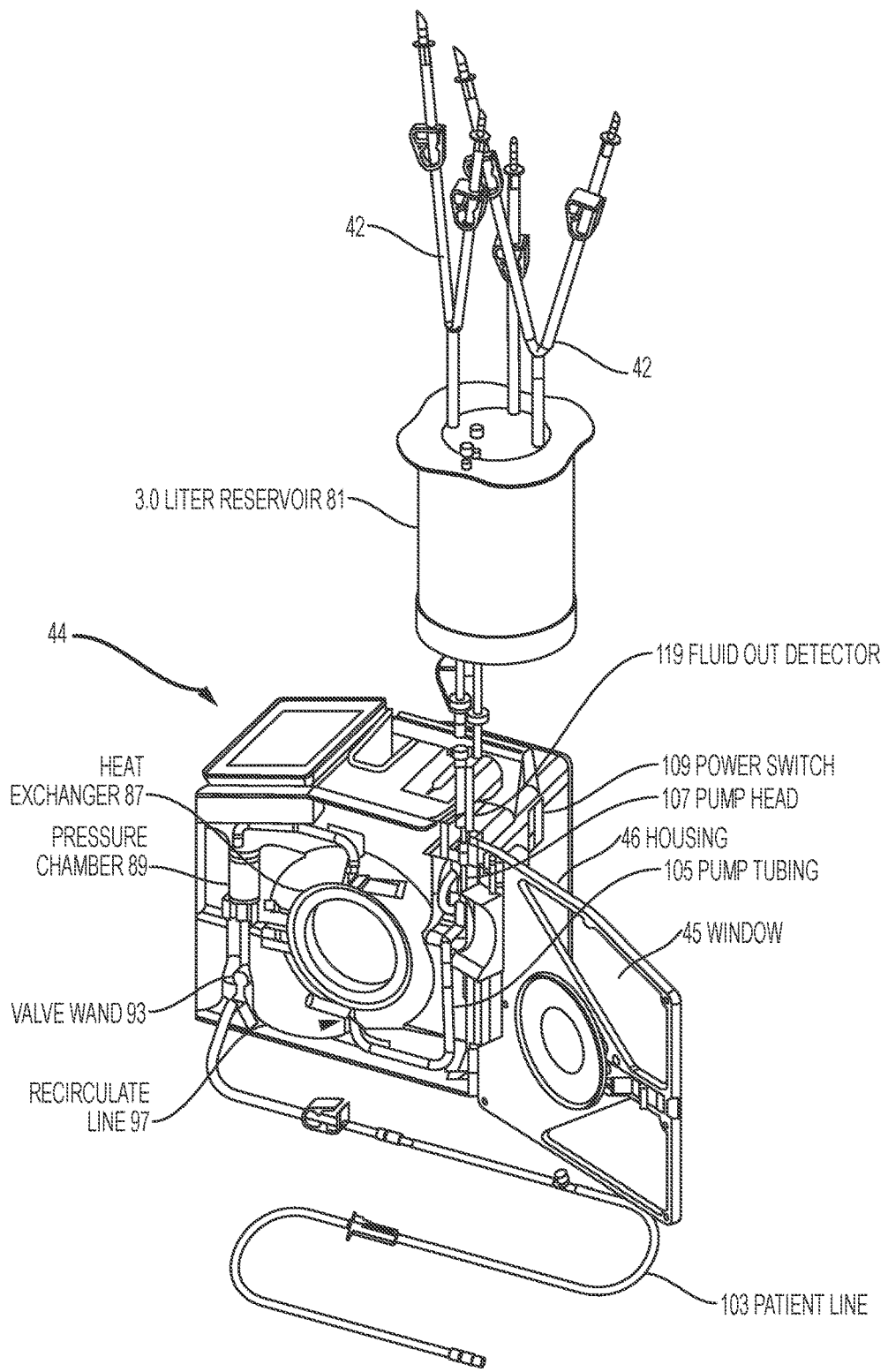
FIG. 12 is a schematic representation of a slack time heating system with an associated disposable set, according to an embodiment of the present invention.

FIG. 12 depicts an exemplary slack-time heating system. The system comprises a large volume reservoir 81 connected to a pump tubing 105 threaded through a roller pump head further connected to a heat exchanger 87. The fluid path continues to a pressure chamber 89 and then directs one path to a patient via a patient line 103 or back to the reservoir 81 via a recirculation line 97.

In certain embodiments, a slack-time heating system comprises a diversion valve 93 that controls the ratio between a flow in a patient line and a flow in a recirculation line. When the diversion valve is in a recirculation position (e.g., the patient line is obstructed, while the recirculation line is opened), the pump 107 will cause fluid in a bubble trap to flow back to the reservoir (e.g., exit from the top).

In certain embodiments, reservoirs of the present disclosure mix unheated fluid and heated fluid.

In certain embodiments, the ratio of a flow in a patient line to a flow in a recirculation line is between 100:1 and 1:100.

In certain embodiments, the slack time heating system utilizes a single flow path as described in the present disclosure.

Vacuum Release Vale

Figure 14A:
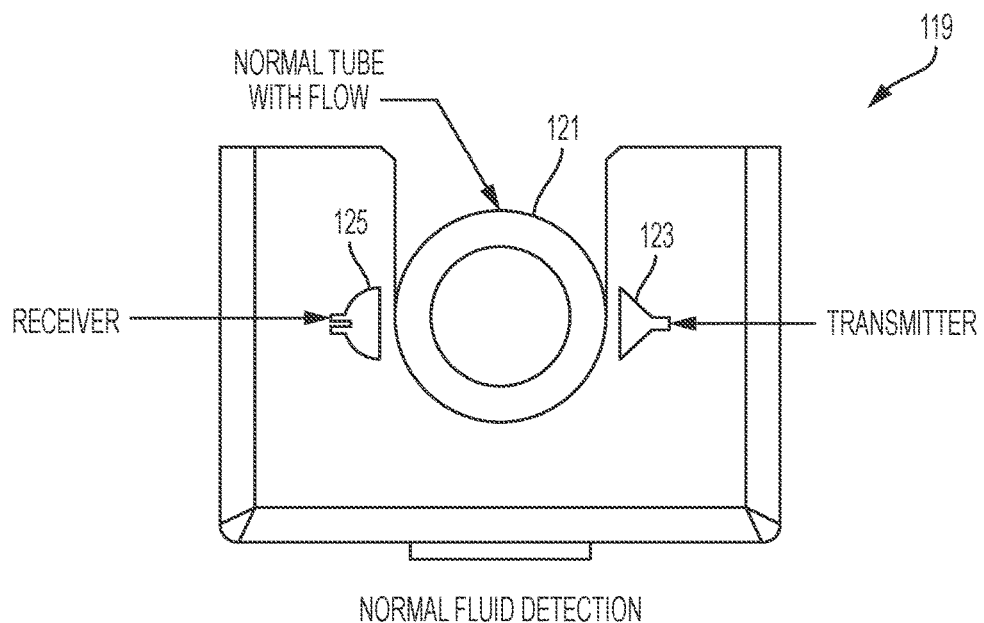
FIGS. 14A-14C demonstrate a sensor for a fluid level in a reservoir, and deformation of an inflow tubing.
Figure 14B:
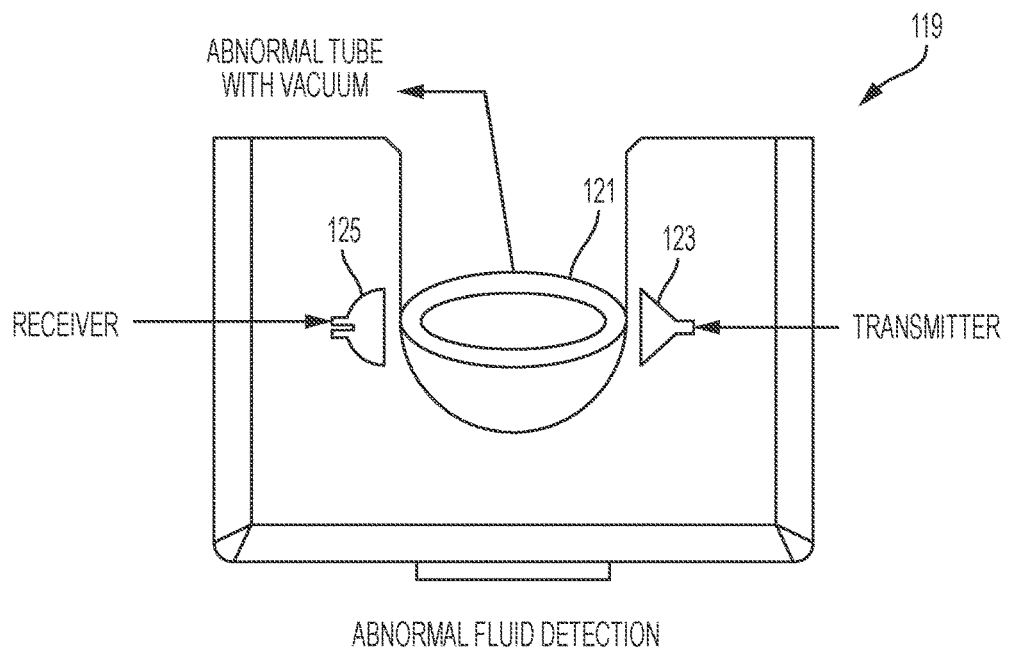
Figure 14C:
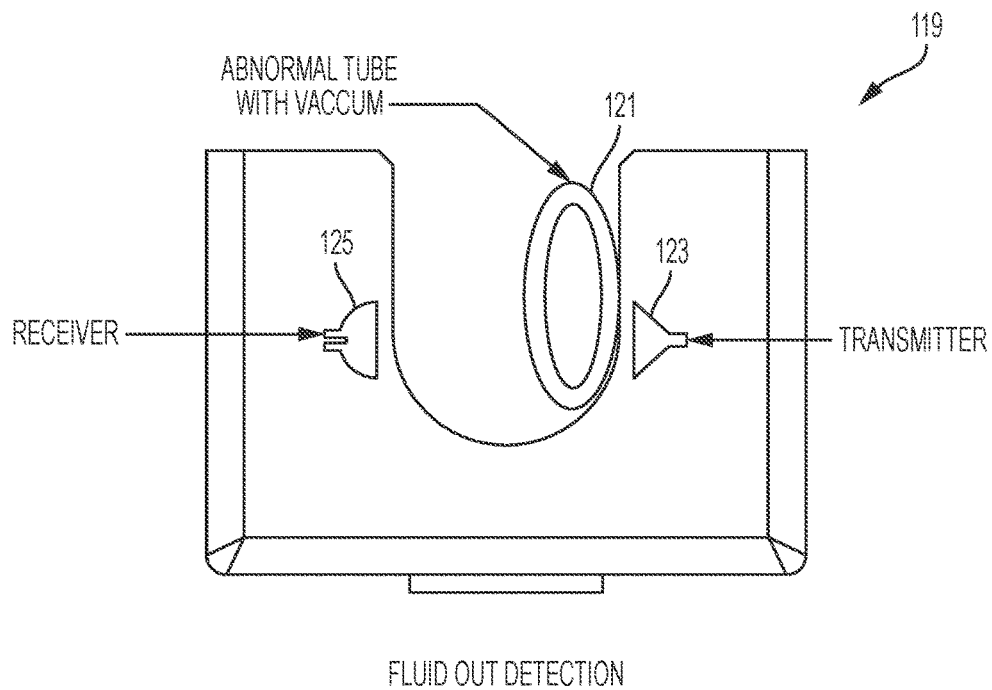

In certain embodiments, a fluid heating system has a sensor (e.g., fluid out sensor) 119 connected to an inflow tubing 121 (e.g., from an infusate reservoir to fluid heaters) to detect if an infusate reservoir is empty. Typically, the sensor comprises a transmitter 123 and a receiver 125, and measures velocity of ultrasound (e.g., ultrasound travels faster through fluids than air) as shown in FIG. 14A. The inflow tubing 121 is located between the transmitter 123 and the receiver 125. When the fluid level in the infusate reservoir is low (or zero), the pressure in the infusate reservoir and the inflow tubing is lower than the atmospheric pressure. Therefore, the non-rigid inlet tubing 121 deforms to minimize the pressure difference. For example, the cross-section area of the inlet tubing reduces, or the cross-section of the inflow tubing becomes elliptic, as shown in FIGS. 14B and 14C. The sensor measures this deformation of the inflow tubing.

The direction of deformation affects detectability by the sensor. For example, a major axis of the elliptic cross-section can be perpendicular to a line between the transmitter and the receiver as shown in FIG. 14C, or parallel to that line as shown in FIG. 14B. If the major axis of the elliptic cross-section is not parallel (e.g., perpendicular) to the line between the transmitter and the receiver, the sensor can measure the deformation properly as the ultrasound travels in air more than before the deformation. However, if the major axis of the elliptic cross-section is parallel to a line between the transmitter and the receiver, the sensor cannot detect the deformation because of lack of air in the ultrasound beam path.

The present disclosure is directed to a fluid heating system that includes a vacuum release valve to prevent the undesired orientation of the deformed inflow tubing. In certain embodiments, the vacuum release valve supply air to the tubing to reduce pressure difference between the inflow tubing and the surroundings, preventing the deformation of the inflow tubing.

Figure 15A:
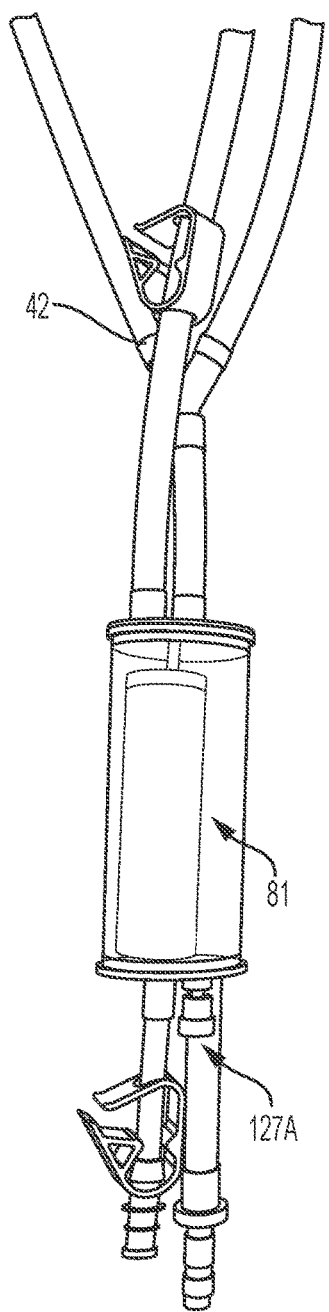
FIGS. 15A-15C depict exemplary disposable set with vacuum release valve, according to an embodiment of the present invention.
Figure 15B:
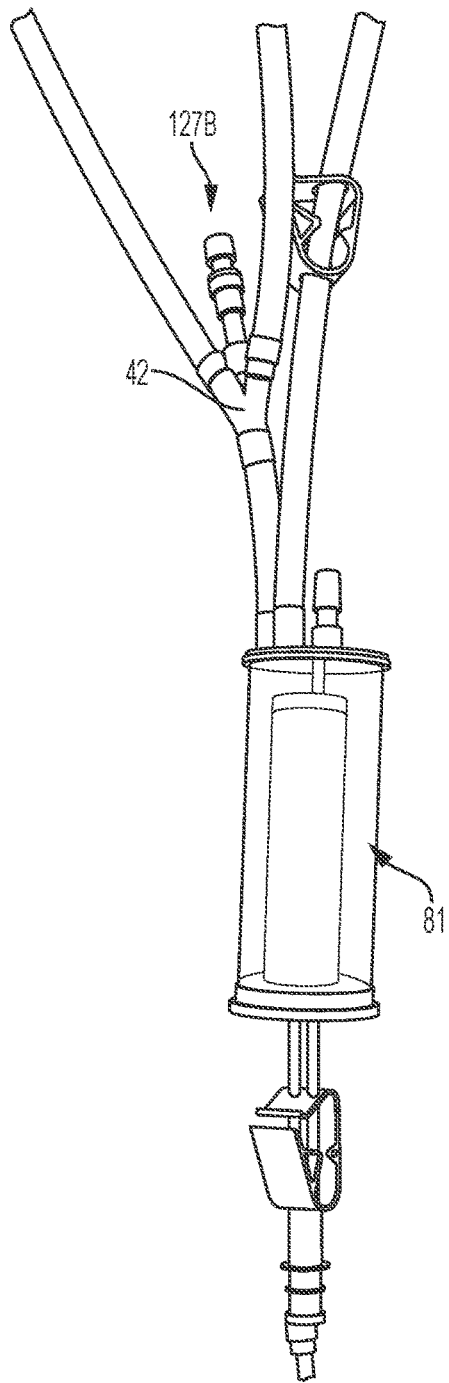
Figure 15C:
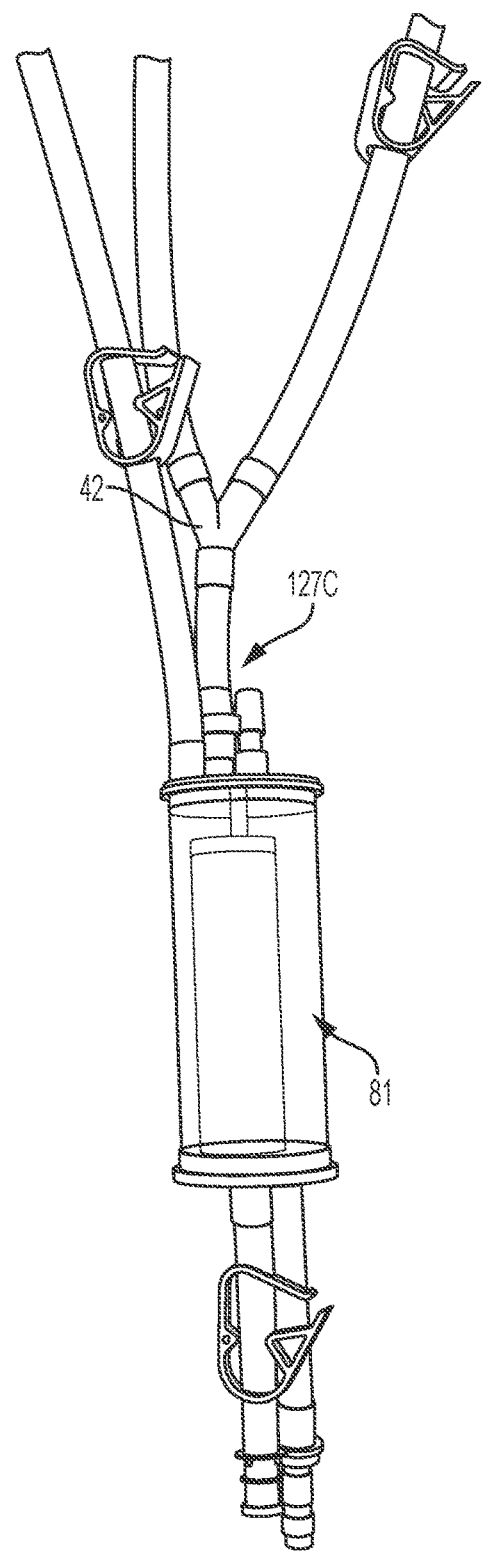

FIGS. 15A-15C depict exemplary disposable sets with vacuum release valves. In certain embodiments, the vacuum release valve 127A is connected on the bottom of the reservoir (FIG. 15A). The inflow tubing and the vacuum release valve may be parallel to each other. In certain embodiments, the vacuum release valve 127C is connected on the bottom of the reservoir (FIG. 15C). In certain embodiments, the vacuum release valve is indirectly connected to the reservoir. The reservoir may comprise a tubing attached to the top of the reservoir (FIG. 15B). The vacuum release valve may be connected to the reservoir through the tubing.

Any type of suitable vacuum release valve may be used in accordance with the disclosure. The vacuum release valve may comprise a housing and a regulator. The vacuum release valve may operate automatically (e.g., without an operator). The vacuum release valve is normally closed (e.g., the vacuum release valve does not allow air into the inflow tubing, e.g., the regulator presses against a portion of the housing, thereby blocking air passage). When the pressure difference between the system (e.g., the reservoir, inflow tubing) and the atmosphere reaches a pre-determined value (e.g., 0.5, 1, 2, 3, 4, 5, 6, 7, 8, 9 or 10 psi), the vacuum release valve opens (e.g., the valve allows air to flow into the system). The pre-determined value may be manipulated by varying an external force applied to the regulator. For example, if the pressure difference between the system (e.g., the reservoir, inflow tubing) and the atmosphere exceeds the applied force per area, the valve opens. The force may be applied mechanically (e.g., spring, diaphragm).

In certain embodiments, the vacuum release valve supplies air to the disposable set when the pressure of the disposable set is about 0.5, 1, 2, 3, 4, 5, 6, 7, 8, 9, or 10 psi lower than atmospheric pressure.

In certain embodiments, the vacuum release valve comprises a filter, and/or a sanitation unit to provide sterile air to the system.

In certain embodiments, a vacuum release valve is included as part of a disposable set.

EXEMPLIFICATION

Single Flow Path

The present example describes, among other things, an exemplary operation of single flow path induction heater with an exemplary spiral inductive tube.

Figure 11:
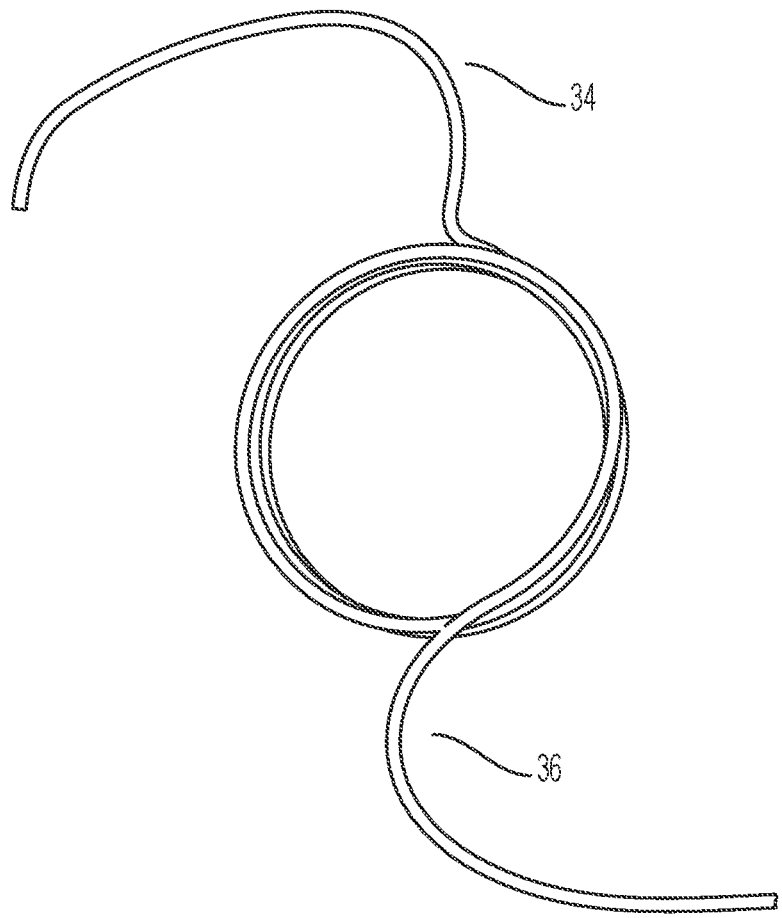
FIG. 11 shows a spiral inductive tube, according to an embodiment of the present invention.

As shown in FIG. 11, aluminum tubing with an inner diameter of ⅛" and an outer diameter of 3/16" was shaped into a circular form to be operated within the Belmont® Rapid Infuser by Belmont. Circular loops with 2.5 overlapping turns and extended tails were created. Copper wire was wrapped around the input and output in order to provide electrical connection with in the tubing. The tails are positioned in a fashion so that the input and output thermal detectors are as close as possible to the input and the output. The spiral inductive tube was successfully installed in the Belmont® Rapid Infuser. The system pumped fluid through the tubing. Temperature of the outlet fluid was increased relative to temperature of the inlet fluid.

Vacuum Release Valve

The present example describes, among other things, exemplary operations of a rapid heating system with exemplary vacuum release valves.

Disposable sets (e.g., The Belmont® 3-Spike Disposable Set) with various vacuum release valves as shown in FIGS. 15A-15C were tested with the Belmont Rapid Infuser. A vacuum release valve was connected to the 4.4 L reservoir (FIG. 15A), a y-connection at the intersection of tubing (FIG. 15B), or onto the filter assembly (FIG. 15C). The modified disposable sets and the unmodified set were then tested. Testing mediums were water, sodium chloride and water at 35.7 grams per 100 mL, and a 50/50 mix of water and glycerin by volume. Each modified disposable set was tested at a wide range of flow rates. While the unmodified set was clamped off as pressure decreased, the vacuum release valve of the modified sets allowed air to be drawn into the set, and did not experience clamping off. Once the reservoir was sufficiently emptied, air would be drawn into the fluid path causing the fluid out detector to register and the machine to turn off properly. The valve worked successfully with all testing mediums and at any flow rate. The addition of the vacuum release valve prevented the improper deformation of tubing.

What is claimed is:

1. A system for heating a fluid, the system comprising:
a conduit defining a central opening;
a primary inductor at least partially within the central opening;
one or more secondary inductors within the conduit;
an inflow tubing connected to the conduit; and
a vacuum release valve,
wherein each of the one or more secondary inductors is substantially parallel, the one or more secondary inductors being separated by gaps,
wherein the primary inductor comprises a coil,
wherein, when the primary inductor is energized, the coil generates magnetic flux passing through the central opening, and
wherein, when pressure in the inflow tubing is lower than atmospheric pressure, the vacuum release valve allows flow of air into the inflow tubing, thereby preventing deformation of the inflow tubing.

2. The system of claim 1, further comprising a reservoir for containing an infusate.

3. The system of claim 2, wherein the vacuum release valve is connected to the reservoir.

4. The system of claim 3, wherein the vacuum release valve is connected to the top of the reservoir.

5. The system of claim 3, wherein the vacuum release valve is connected to the bottom of the reservoir.

6. The system of claim 2, wherein the reservoir further comprises a tubing attached to the top of the reservoir, and the vacuum release valve is connected to the reservoir through the tubing.

7. The system of claim 1, wherein the vacuum release valve allows flow of air into the inflow tubing when pressure in the inflow tubing is 2 psi lower than atmospheric pressure.

8. The system of claim 1, wherein the conduit provides a single fluid flow path.

9. The system of claim 8, wherein the single fluid flow path has a conformation such that fluid is not in contact with the primary inductor.

10. The system of claim 1, further comprising a fluid separator comprising an inlet nozzle and an outlet nozzle, wherein the inlet nozzle directs an inlet flow to the conduit through the fluid separator and the outlet nozzle receives an outlet flow from the conduit through the fluid separator.

11. The system of claim 1, wherein the conduit comprises a plurality of spacers which provides the gaps between the one or more secondary inductors.

12. The system of claim 1, wherein the one or more secondary inductors transfers heat to fluid within the conduit.

13. The system of claim 1, further comprising a bubble trap for removing air bubbles from fluid flowing through the system.

14. A disposable unit of a system for heating a fluid, the disposable unit comprising:
a conduit, defining a central opening;
one or more secondary inductors within the conduit;
an inflow tubing connected to the conduit; and
a vacuum release valve;
wherein each of the one or more secondary inductors is substantially parallel,
wherein the one or more secondary inductors being separated by gaps,
wherein, when pressure in the inflow tubing is lower than atmospheric pressure, the vacuum release valve allows flow of air into the inflow tubing, thereby preventing deformation of the inflow tubing and
wherein the conduit provides a single fluid flow path.

15. The disposable unit of claim 14, further comprising a reservoir for containing an infusate.

16. The disposable unit of claim 15, wherein the vacuum release valve is connected to the reservoir.

17. The disposable unit of claim 16, wherein the vacuum release valve is connected to the top of the reservoir.

18. The disposable unit of claim 16, wherein the vacuum release valve is connected to the bottom of the reservoir.

19. The disposable unit of claim 15, wherein the reservoir further comprises a tubing attached to the top of the reservoir, and the vacuum release valve is connected to the reservoir through the tubing.

20. The disposable unit of claim 14, further comprising a fluid separator comprising an inlet nozzle and an outlet nozzle.

21. The disposable unit of claim 14, further comprising a bubble trap for removing air bubbles from fluid flowing through the system.

* * * * *